US010549063B2

(12) United States Patent
Desilva et al.

(10) Patent No.: US 10,549,063 B2
(45) Date of Patent: *Feb. 4, 2020

(54) MODULAR FLOW CASSETTE

(71) Applicant: Vyaire Medical Capital LLC, Yorba Linda, CA (US)

(72) Inventors: Adrian D. Desilva, Riverside, CA (US); Huy Thanh Vu, Westminster, CA (US); Richard Le, Oceanside, CA (US); Jeffrey Harold Miller, Irvine, CA (US); Hector Gonzalez, Corona, CA (US); Raul Valdez, Eastvale, CA (US); Chiun Wang, Cypress, CA (US)

(73) Assignee: Vyaire Medical Capital LLC, Yorba Linda, CA (US)

( * ) Notice: Subject to any disclaimer, the term of this patent is extended or adjusted under 35 U.S.C. 154(b) by 371 days.

This patent is subject to a terminal disclaimer.

(21) Appl. No.: 15/652,025

(22) Filed: Jul. 17, 2017

(65) Prior Publication Data

US 2017/0312473 A1    Nov. 2, 2017

Related U.S. Application Data

(63) Continuation of application No. 13/931,566, filed on Jun. 28, 2013, now Pat. No. 9,707,369.

(51) Int. Cl.
*A61M 16/12* (2006.01)
*G01F 1/50* (2006.01)
(Continued)

(52) U.S. Cl.
CPC ............. *A61M 16/12* (2013.01); *G01F 1/50* (2013.01); *A61M 16/106* (2014.02);
(Continued)

(58) Field of Classification Search
CPC .......... A61M 16/0003; A61M 16/0027; A61M 16/003; A61M 16/0033; A61M 16/0057;
(Continued)

(56) References Cited

U.S. PATENT DOCUMENTS 2,037,880 A    4/1936    Charavay
2,510,125 A    6/1950    Meakin
(Continued)

FOREIGN PATENT DOCUMENTS

CN    1041204 A    4/1990
CN    101225881 A    7/2008
(Continued)

OTHER PUBLICATIONS

Australian Examination Report No. 1 for Application No. 2014302304, dated Aug. 15, 2017, 3 pages.
(Continued)

*Primary Examiner* — Joseph D. Boecker
(74) *Attorney, Agent, or Firm* — Morgan, Lewis & Bockius LLP

(57) ABSTRACT

A flow cassette has a housing with an inlet and an outlet and a passage therebetween. The flow cassette also has a temperature sensor disposed within the passage and configured to measure the temperature of a fluid flowing through the passage, a flow rate sensor disposed within the passage and configured to measure a flow rate of the fluid flowing through the passage, and a processor coupled to the temperature sensor and flow rate sensor. The processor is configured to accept measurements of temperature and flow rate from the temperature sensor and flow rate sensor, respectively, and provide a compensated flow rate.

19 Claims, 5 Drawing Sheets

(51) Int. Cl.
  *A61M 16/00* (2006.01)
  *A61M 16/10* (2006.01)
  *A61M 16/20* (2006.01)

(52) U.S. Cl.
  CPC ... *A61M 16/208* (2013.01); *A61M 2016/0027* (2013.01); *A61M 2016/0039* (2013.01); *A61M 2205/12* (2013.01); *A61M 2205/3317* (2013.01); *A61M 2205/3368* (2013.01); *A61M 2205/50* (2013.01); *A61M 2205/6018* (2013.01); *A61M 2205/6054* (2013.01); *A61M 2205/702* (2013.01)

(58) Field of Classification Search
  CPC .... A61M 16/12; A61M 16/20; A61M 16/201; A61M 16/202; A61M 2016/0039; A61M 2016/102; A61M 2205/12; A61M 2205/128; A61M 2205/14; A61M 2205/3331; A61M 2205/3334; A61M 2205/3337; A61M 2205/3341; A61M 2205/3344; A61M 2205/3368; A61M 2205/50; A61M 2205/6018; A61M 2205/6054; A61M 2205/702; G01F 1/36; G01F 1/50; A61B 5/087; A61B 2018/00863
  USPC ............ 128/202.27, 203.14, 203.24, 204.18, 128/204.21–204.25, 205.24; 600/538
  See application file for complete search history.

(56) References Cited

U.S. PATENT DOCUMENTS

| | | |
|---|---|---|
| 2,634,311 A | 4/1953 | Darling |
| 3,140,042 A | 7/1964 | Noriyoshi |
| 3,673,541 A | 6/1972 | Volinskie |
| 3,690,460 A * | 9/1972 | Lindboe .............. B01D 27/103 210/130 |
| 3,776,215 A | 12/1973 | Howard et al. |
| 3,788,765 A | 1/1974 | Rusak |
| 4,167,369 A | 9/1979 | Ishihara |
| 4,243,357 A | 1/1981 | Flynn et al. |
| 4,381,668 A | 5/1983 | Sato et al. |
| 4,543,041 A | 9/1985 | French et al. |
| 4,562,744 A | 1/1986 | Hall et al. |
| 4,571,801 A | 2/1986 | Ewing |
| 4,649,760 A | 3/1987 | Wedding |
| 4,754,651 A | 7/1988 | Shortridge et al. |
| 4,763,645 A | 8/1988 | Kapp |
| 4,809,742 A | 3/1989 | Grau |
| 4,825,904 A | 5/1989 | Grau et al. |
| 4,909,545 A | 3/1990 | Hohol |
| 4,971,054 A * | 11/1990 | Andersson .......... A61M 16/208 128/207.14 |
| 4,978,281 A | 12/1990 | Conger, IV |
| 5,064,346 A | 11/1991 | Atarashi et al. |
| 5,127,400 A | 7/1992 | DeVries et al. |
| 5,190,068 A | 3/1993 | Philbin |
| 5,265,594 A | 11/1993 | Olsson et al. |
| 5,277,196 A | 1/1994 | Hankinson et al. |
| 5,295,397 A | 3/1994 | Hall et al. |
| 5,331,995 A | 7/1994 | Westfall et al. |
| 5,339,807 A | 8/1994 | Carter |
| 5,365,795 A | 11/1994 | Brower, Jr. |
| 5,461,932 A | 10/1995 | Hall et al. |
| 5,478,206 A | 12/1995 | Prahst |
| 5,537,992 A | 7/1996 | Bjoernstijerna et al. |
| 5,572,992 A | 11/1996 | Kankkunen et al. |
| 5,604,681 A | 2/1997 | Koeninger |
| 5,606,236 A | 2/1997 | Tennies et al. |
| 5,771,884 A | 6/1998 | Yarnall et al. |
| 5,918,596 A | 7/1999 | Heinonen |
| 5,954,051 A | 9/1999 | Heinonen et al. |
| 6,017,315 A | 1/2000 | Starr et al. |
| 6,139,262 A | 10/2000 | Ravidranath |
| 6,151,557 A | 11/2000 | Broden et al. |
| 6,422,092 B1 | 7/2002 | Morrison et al. |
| 6,422,256 B1 | 7/2002 | Balazy et al. |
| 6,553,923 B2 | 4/2003 | Gatley, Jr. |
| 6,578,818 B1 | 6/2003 | Krimmer et al. |
| 6,609,431 B1 | 8/2003 | Tietsworth et al. |
| 6,622,724 B1 | 9/2003 | Truitt et al. |
| 6,820,620 B2 | 11/2004 | Rochat |
| 6,945,123 B1 | 9/2005 | Kuehl et al. |
| 7,107,834 B2 | 9/2006 | Meneghini et al. |
| 7,121,139 B2 | 10/2006 | Shajii et al. |
| 7,185,674 B2 * | 3/2007 | Taylor ...................... A62B 9/02 128/202.27 |
| 7,636,640 B2 | 12/2009 | Wang et al. |
| 7,819,022 B2 | 10/2010 | Hope |
| 7,826,986 B2 | 11/2010 | McDonald |
| 8,215,157 B2 | 7/2012 | Wang et al. |
| 8,504,318 B2 | 8/2013 | Mendelson et al. |
| 9,003,877 B2 | 4/2015 | Qasimi et al. |
| 2002/0085952 A1 | 7/2002 | Ellingboe et al. |
| 2002/0198668 A1 | 12/2002 | Lull et al. |
| 2003/0106554 A1 | 6/2003 | de Silva et al. |
| 2003/0220605 A1 | 11/2003 | Bowman et al. |
| 2004/0074311 A1 | 4/2004 | Lull et al. |
| 2004/0177703 A1 | 9/2004 | Schumacher et al. |
| 2004/0187871 A1 | 9/2004 | Kimmel et al. |
| 2005/0004534 A1 | 1/2005 | Lockwood et al. |
| 2005/0241412 A1 | 11/2005 | Tison et al. |
| 2006/0079765 A1 | 4/2006 | Neer et al. |
| 2006/0144163 A1 | 7/2006 | Friberg |
| 2006/0162466 A1 | 7/2006 | Wargo et al. |
| 2006/0236781 A1 | 10/2006 | Ohmi et al. |
| 2007/0193369 A1 | 8/2007 | Evans et al. |
| 2007/0265877 A1 | 11/2007 | Rice et al. |
| 2007/0277824 A1 | 12/2007 | Aylsworth et al. |
| 2008/0059084 A1 | 3/2008 | Wang et al. |
| 2008/0092891 A1 | 4/2008 | Cewers |
| 2008/0105259 A1 | 5/2008 | de Silva et al. |
| 2008/0283062 A1 | 11/2008 | Esposito, Jr. |
| 2009/0038615 A1 | 2/2009 | Bradley |
| 2009/0084164 A1 * | 4/2009 | Lowery ................... G01F 1/36 73/38 |
| 2009/0093774 A1 | 4/2009 | Wang et al. |
| 2009/0095068 A1 | 4/2009 | Redemann et al. |
| 2009/0113996 A1 | 5/2009 | Wang et al. |
| 2009/0293634 A1 | 12/2009 | Ong |
| 2009/0326839 A1 | 12/2009 | Rogers et al. |
| 2010/0031737 A1 | 2/2010 | Saito et al. |
| 2010/0139660 A1 | 6/2010 | Adahan |
| 2010/0229967 A1 | 9/2010 | Yasuda et al. |
| 2010/0236552 A1 | 9/2010 | Kwok et al. |
| 2010/0307490 A1 * | 12/2010 | Broborg .............. A61M 16/209 128/203.12 |
| 2011/0100364 A1 | 5/2011 | Faram |
| 2011/0126834 A1 | 6/2011 | Winter et al. |
| 2011/0126837 A1 | 6/2011 | Winter et al. |
| 2011/0301867 A1 | 12/2011 | Davis et al. |
| 2012/0065533 A1 | 3/2012 | Carrillo, Jr. et al. |
| 2012/0085349 A1 | 4/2012 | Tobias et al. |
| 2012/0185102 A1 | 7/2012 | Skoglund et al. |
| 2012/0204874 A1 | 8/2012 | Sofranko |
| 2012/0226449 A1 | 9/2012 | Delache et al. |
| 2012/0229272 A1 | 9/2012 | Jacob et al. |
| 2012/0285454 A1 | 11/2012 | Nibu et al. |
| 2012/0285455 A1 | 11/2012 | Varga et al. |
| 2012/0318383 A1 | 12/2012 | Yasuda et al. |
| 2013/0036806 A1 | 2/2013 | Kohno |
| 2013/0079667 A1 | 3/2013 | Berkcan et al. |
| 2013/0153040 A1 | 6/2013 | Goto et al. |
| 2013/0220314 A1 | 8/2013 | Bottom |
| 2013/0247905 A1 | 9/2013 | Miller et al. |
| 2014/0054479 A1 | 2/2014 | Shen |
| 2014/0066880 A1 | 3/2014 | Prince et al. |
| 2014/0182590 A1 | 7/2014 | Platt et al. |
| 2014/0251322 A1 | 9/2014 | Miller |
| 2015/0020807 A1 | 1/2015 | Kimmel |

(56) References Cited

U.S. PATENT DOCUMENTS

| | | |
|---|---|---|
| 2015/0096560 A1 | 4/2015 | Klenner et al. |
| 2015/0143921 A1 | 5/2015 | Postberg et al. |
| 2016/0256646 A1 | 9/2016 | Vazales |

FOREIGN PATENT DOCUMENTS

| | | |
|---|---|---|
| CN | 101687086 A | 3/2010 |
| CN | 102155570 A | 8/2011 |
| CN | 202366282 U | 8/2012 |
| CN | 102686888 A | 9/2012 |
| CN | 102927292 A | 2/2013 |
| CN | 103041492 A | 4/2013 |
| CN | 202870631 U | 4/2013 |
| EP | 0829793 A1 | 3/1998 |
| EP | 1127583 A2 | 8/2001 |
| EP | 1658874 A2 | 5/2006 |
| EP | 2402616 A1 | 1/2012 |
| JP | S5659 A | 1/1981 |
| JP | 2006519997 A | 8/2006 |
| JP | 2008511358 A | 4/2008 |
| JP | 2009508647 A | 3/2009 |
| WO | WO-0138832 A2 | 5/2001 |
| WO | WO-2006024532 A1 | 3/2006 |
| WO | WO-2011055254 A1 | 5/2011 |
| WO | WO-2013002699 A1 | 1/2013 |

OTHER PUBLICATIONS

Chinese Office Action for Application No. 201480036606.9, dated Sep. 2, 2016, 6 pages excluding translation.

Chinese Office Action for Application No. 201480036971.X, dated Oct. 8, 2016, 10 pages excluding English translation.

Chinese Office Action for Application No. 201480037090.X, dated Sep. 26, 2016, 6 pages excluding English translation.

Chinese Office Action for Application No. 201480037104.8, dated Nov. 17, 2016, 5 pages excluding English translation.

International Search Report and Written Opinion for Application No. PCT/US2015/038155, dated Dec. 17, 2015, 18 pages.

International Search Report and Written Opinion for Application No. PCT/US2015/038157, dated Nov. 5, 2015, 12 pages.

International Search Report and Written Opinion for International Application No. PCT/US2014/044737, dated May 19, 2015, 18 pages.

International Search Report and Written Opinion in PCT Application No. PCT/US2014/044438 dated Oct. 28, 2014, 11 pages.

International Search Report and Written Opinion in PCT Application No. PCT/US2014/044441 dated Oct. 31, 2014, 12 pages.

International Search Report and Written Opinion in PCT Application No. PCT/US2014/044442 dated Nov. 3, 2014, 10 pages.

International Search Report and Written Opinion in PCT Application No. PCT/US2014/044724 dated Oct. 21, 2014, 12 pages.

International Search Report for International Application No. PCT/US2014/044743, dated Jan. 22, 2015, 6 pages.

Invitation to Pay Additional Fees and Partial Search Report for Application No. PCT/US2015/038155, dated Oct. 7, 2015, 7 pages.

Invitation to Pay Additional Fees in International Application No. PCT/US2014/044737 dated Oct. 28, 2014, 7 pages.

Invitation to Pay Additional Fees in PCT Application No. PCT/US2014/044743 dated Oct. 21, 2014, 7 pages.

Chinese Office Action for Application No. 201480035877.2, dated Feb. 1, 2018, 12 pages excluding English translation.

Japanese Office Action for Application No. 2016-524216, dated May 23, 2018, 11 pages.

\* cited by examiner

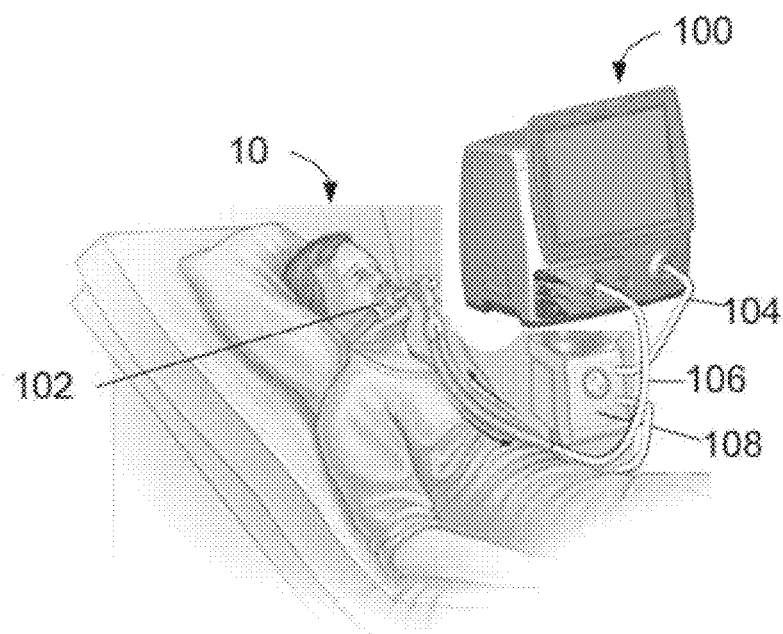
*FIG. 1*
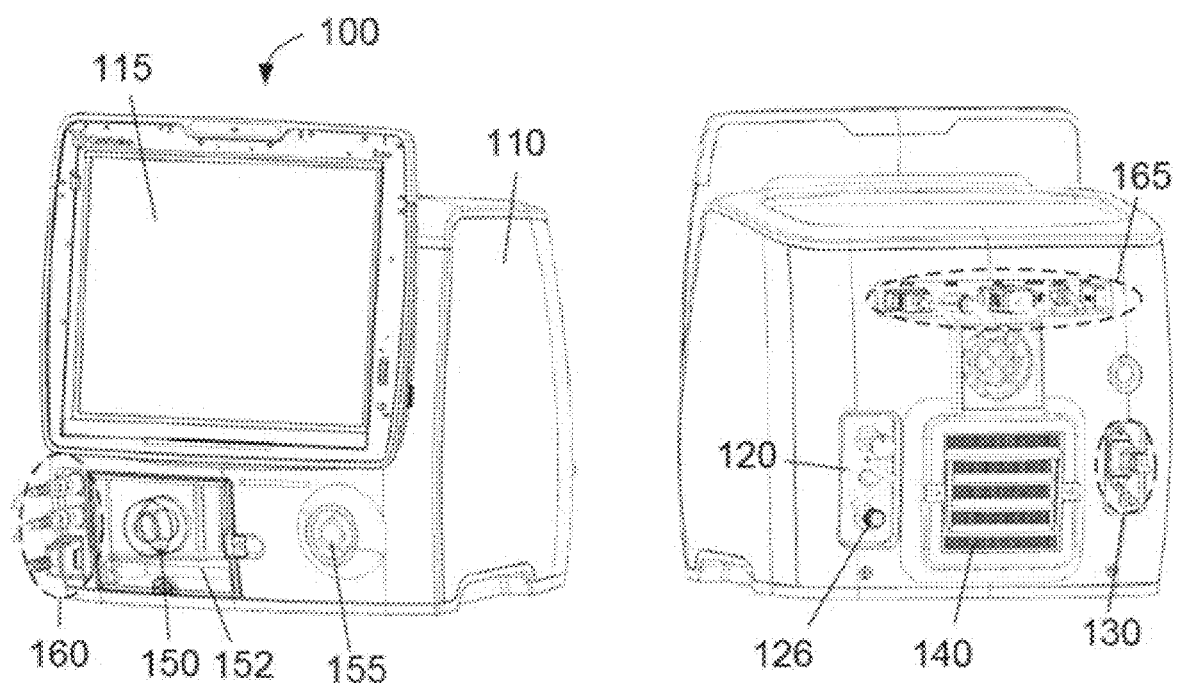
*FIG. 2A*  *FIG. 2B*

MODULAR FLOW CASSETTE

CROSS-REFERENCES TO RELATED APPLICATIONS

This application is a continuation of U.S. patent application Ser. No. 13/931,566, filed on Jun. 28, 2013, entitled "MODULAR FLOW CASSETTE," the disclosure of which is incorporated herein by reference in its entirety for all purposes.

BACKGROUND

The present disclosure generally relates to gas mixing and, in particular, to accurate control of the flow rate of a gas flow from a pressurized source.

Patients with respiratory injury, such as chronic respiratory failure, may be provided with a respirator to assist with their breathing or, in severe cases, take over the breathing function entirely. Respirators typically provide a flow of air, or other breathing gases, at an elevated pressure during an inhalation interval, followed by an exhalation interval where the pressurized air is diverted so that the air within the patient's lungs can be naturally expelled.

Conventional respirators may be configured to accept one or more breathing gases, for example "pure oxygen" or "heliox 80/20" (a mixture of 80% helium with 20% oxygen) from external sources. The exact gas mixture delivered to the patient, however, may be a mixture of various breathing gases since the specific percentage required for a particular patient may not be commercially available and must be custom mixed in the respirator.

It is important to provide precisely the specified flow rate of gas to the patient, particularly for neonatal patients whose lungs are small and very susceptible to damage from over-inflation.

SUMMARY

It is advantageous to provide a modular flow cassette that provides accurate flow measurements of a variety of gases and gas mixtures over a range of temperatures and flow rates.

In certain embodiments, a flow cassette is disclosed that has a housing with an inlet and an outlet and a passage therebetween. The flow cassette also has a temperature sensor disposed within the passage and configured to measure the temperature of a fluid flowing through the passage, a flow rate sensor disposed within the passage and configured to measure a flow rate of the fluid flowing through the passage, and a processor coupled to the temperature sensor and flow rate sensor. The processor is configured to accept measurements of temperature and flow rate from the temperature sensor and flow rate sensor, respectively, and provide a compensated flow rate.

In certain embodiments, a method of configuring a ventilator for a patient is disclosed. The method comprising the step of installing a flow cassette into a ventilator. The flow cassette has a housing with an inlet and an outlet and a passage therebetween. The flow cassette also has a temperature sensor disposed within the passage and configured to measure the temperature of a fluid flowing through the passage, a flow rate sensor disposed within the passage and configured to measure a flow rate of the fluid flowing through the passage, and a processor coupled to the temperature sensor and flow rate sensor. The processor is configured to accept measurements of temperature and flow rate from the temperature sensor and flow rate sensor, respectively, and provide a compensated flow rate.

In certain embodiments, a ventilator is disclosed that has an output flow channel configured to mate with a supply limb, an input flow channel configured to accept a gas from a source, and a flow cassette that has a housing with an inlet and an outlet and a passage therebetween. The flow cassette also has a temperature sensor disposed within the passage and configured to measure the temperature of a fluid flowing through the passage, a flow rate sensor disposed within the passage and configured to measure a flow rate of the fluid flowing through the passage, and a processor coupled to the temperature sensor and flow rate sensor. The processor is configured to accept measurements of temperature and flow rate from the temperature sensor and flow rate sensor, respectively, and provide a compensated flow rate.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings:

FIG. 1 depicts a patient using an exemplary ventilator according to certain aspects of the present disclosure.

FIGS. 2A and 2B are front and rear views of the exemplary ventilator according to certain aspects of the present disclosure.

DETAILED DESCRIPTION

Figure 3:
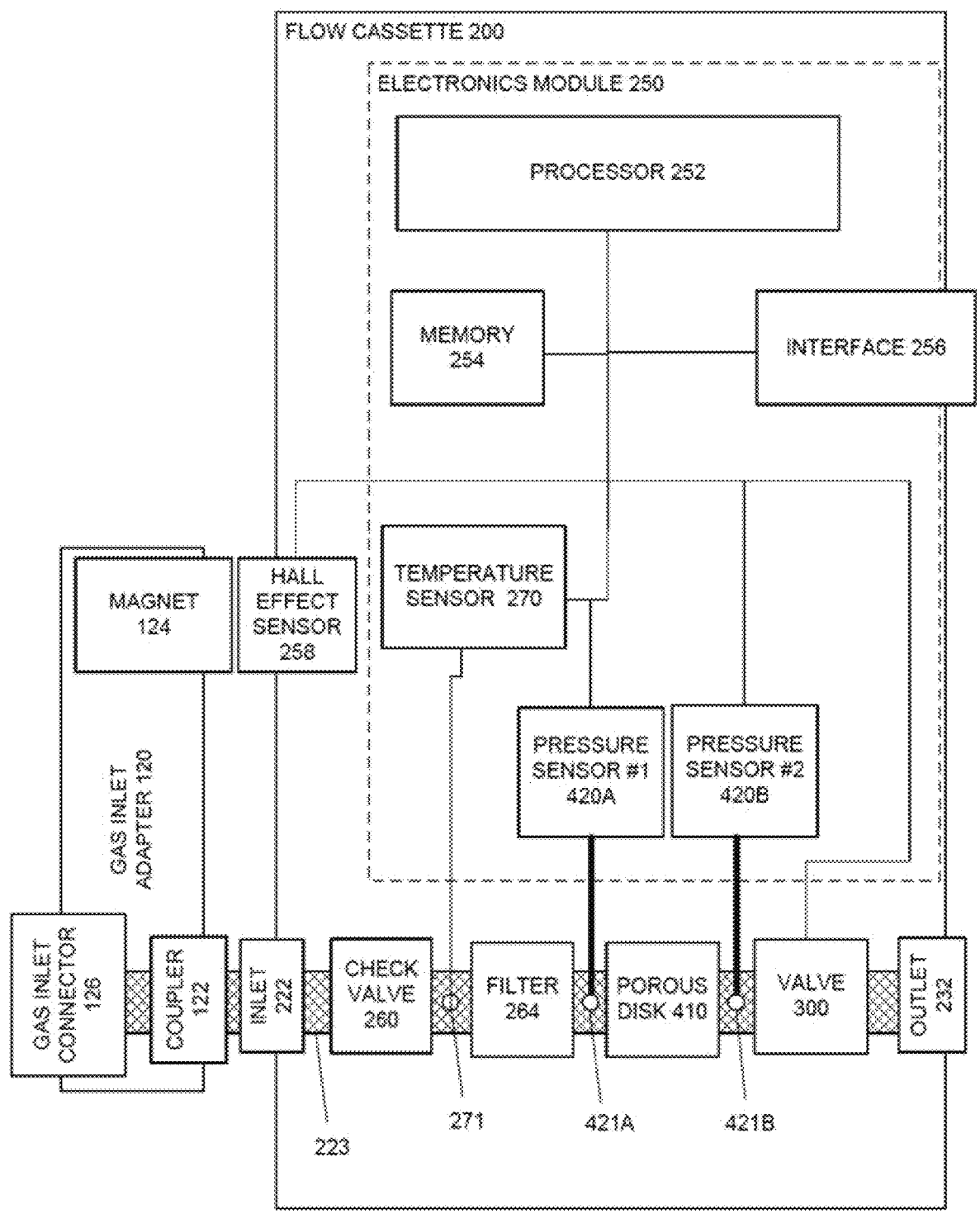
FIG. 3 is a block diagram of an exemplary flow cassette according to certain aspects of the present disclosure.

It is advantageous to provide a modular flow cassette that provides accurate flow measurements of a variety of gases and gas mixtures over a range of temperatures and flow rates.

The disclosed systems and methods of measuring flow rates and compensating for the composition of the gas or gas mixture as well as the temperature of the measured gas provides increased accuracy compared to flow measurements made within conventional ventilators.

In the following detailed description, numerous specific details are set forth to provide a full understanding of the present disclosure. It will be apparent, however, to one ordinarily skilled in the art that embodiments of the present disclosure may be practiced without some of the specific details. In other instances, well-known structures and techniques have not been shown in detail so as not to obscure the disclosure. In the referenced drawings, like numbered elements are the same or essentially similar. Reference numbers may have letter suffixes appended to indicate separate instances of a common element while being referred to generically by the same number without a suffix letter.

While the discussion herein is directed to a ventilator for use in a hospital, the disclosed concepts and methods may be applied to environments, such as a home or long-term care facility, and other fields, such as deep-sea diving, that would benefit from accurate flow measurement of a variety of gas mixtures. Those of skill in the art will recognize that these same features and aspects may also be applied to the sensing and control of other fluids besides medical gases.

Within this document, the term "heliox" means a mixture of oxygen and helium. The mixture may contain a designated percentage of each gas, for example "heliox 70/30" containing approximately 70% helium and 30% oxygen. Heliox may contain trace amounts of other gases.

Within this document, the term "gas" shall be interpreted to mean both a single material in gaseous form, for example oxygen, and a mixture of two or more gases, for example air or heliox. A gas may include water or other liquids in the form of vapor or suspended droplets. A gas may also include solid particulates suspended in the gas.

Within this document, the term "pure," when used with reference to a gas, means that the gas meets commonly accepted medical standards for purity and content.

Within this document, the phrase "temperature sensor" means a device configured to measure temperature and provide a signal that is related to the measured temperature. A temperature sensor may include electronics to provide a drive current or voltage and/or measure a current or voltage. The electronics may further include conditioning and conversion circuitry and/or a processor to convert the measured value to a signal that may be in analog or digital form.

Within this document, the phrase "pressure sensor" means a device configured to measure a gas pressure and provide a signal that is related to the measured pressure. A pressure sensor may include electronics to provide a drive current or voltage and/or measure a current or voltage. The electronics may further include conditioning and conversion circuitry and/or a processor to convert the measured value to a signal that may be in analog or digital form. The pressure may be provided in absolute terms or "gauge" pressure, i.e. relative to ambient atmospheric pressure.

Within this document, the phrase "Hall Effect sensor" means a device configured to detect the presence of a magnet or other magnetic element without making physical contact (non-contacting). A Hall Effect sensor may include electronics to provide a drive current or voltage and/or measure a current or voltage. The electronics may further include conditioning and conversion circuitry and/or a processor to convert the measured value to a signal that may be in analog or digital form.

FIG. 1 depicts a patient 10 using an exemplary ventilator 100 according to certain aspects of the present disclosure. In this example, the ventilator 100 is connected to the patient 10 through a supply tube or "limb" 104 and a return or exhaust limb 106. There may be a conditioning module 108 coupled to the supply limb 104 that may, for example, warm or humidify the air passing through the supply limb 104. The supply and exhaust limbs 104, 106 are both coupled to a patient interface device 102 that, in this example, is a mask that fits over the mouth of the patient 10. In other embodiments (not shown in FIG. 1), the patient interface device 102 may include a nasal mask, an intubation device, or any other breathing interface device as known to those of skill in the art.

FIGS. 2A and 2B are front and rear views of an exemplary ventilator 100 according to certain aspects of the present disclosure. The ventilator 100 has a housing 110 with an attached user interface 115 that, in certain embodiments, comprises a display and a touchscreen. In FIG. 2A, it can be seen that the front of the housing 110 includes a supply port 155 for a supply limb, such as supply limb 104 in FIG. 1, and a return port 150 for a exhaust limb, such as the exhaust limb 106 in FIG. 1. The return port 150 may be mounted over an access door 152 that provides access to a filter (not visible in FIG. 2A) that filters and absorbs moisture from the exhaled breath of the patient 10. In certain embodiments, there may also be a front connection panel 160 for connection to, for example, external instruments, sensors, or sensor modules.

FIG. 2B shows a rear view of the ventilator 100 with a gas inlet adapter 120 with an inlet connector 126, an air intake port 140, and a power interface 130 that may include a power plug connector and a circuit breaker reset switch. There may also be a rear interface panel 165 for connection to external instruments or a network interface cable. The flow cassette 200 is installed within the housing 110 behind the gas inlet adapter 120 and in fluid communication between the inlet connector 126 shown in FIG. 2B and the supply port 155 shown in FIG. 2A.

FIG. 3 is a block diagram of an exemplary flow cassette 200 according to certain aspects of the present disclosure. The flow cassette 200 includes an inlet 222 that is configured to sealingly mate with an input flow channel, for example a coupler 122 of the gas inlet adapter 120. The gas inlet adapter 120 also has an inlet connector 126 that is fluidly connected to the coupler 122. Various breathing gases and gas mixtures are associated with individually unique connector types, sizes, and configurations, wherein the association is generally recognized in the medical industry. Each gas inlet adapter 120 has one or more inlet connectors 126 that are adapted to respectively accept a connector that is unique to a certain type of gas or gas mixture. The gas inlet adapter 120 may include one or more magnets 124 wherein the number and placement of magnets 124 are uniquely associated with the inlet connector 126 that will be coupled to the inlet 222 of the flow cassette 200 when that gas inlet adapter 120 is installed in a ventilator 100 and thereby mated with the flow cassette 200. In certain embodiments, the gas inlet adapter 120 may be configured to accept one or more of a standard composition of ambient air, a pure oxygen, and a heliox gas mixture.

The inlet 222 is fluidly connected to a passage 223 that runs through the flow cassette 200 to an outlet 232 that is configured to sealingly mate with an output flow channel of the ventilator 100 that, for example, leads to the supply limb 104 in FIG. 1. In this example embodiment, there are several elements disposed along the passage 223, including a check valve 260, a filter 264, a porous disk 410 and a valve 300. In certain embodiments, some of these elements may be omitted or arranged in a different order along the passage 223. These elements are discussed in greater detail with respect to FIGS. 5A and 5B. In this embodiment, the flow cassette 200 also includes a Hall Effect sensor 258 configured to detect the number and placement of the magnets 124 of the gas inlet adapter 120. By comparing the detected number and placement of the magnets 124 to stored information associating the number and placement of the magnets 124 with gases that will be accepted by the inlet connector that is coupled to the inlet of the flow cassette 200, the processor 252 can automatically determine what gas will be provided through the gas inlet adapter 120 as installed in the ventilator 100. In other embodiments, the gas inlet adapter 120 may include another type of indicator, for example a machine-readable element, that is associated with the configuration of the gas inlet adapter 120 and the flow cassette 200 may include a sensor that is capable of reading the machine-readable element and thereby automatically detecting the configuration of the gas inlet adapter 120.

The flow cassette 200 includes an electronics module 250. In certain embodiments, the electronics module 250 includes a temperature sensor 270 that has a temperature sensing element 271 disposed in the passage 223. The electronics module 250 also includes pressure sensors 420A and 420B that are respectively connected through passages to ports 421A and 421B in the passage 223 that are disposed on opposite sides of the porous disk 410.

The electronics module 250 also includes a flow cassette processor 252 that is connected to a memory 254 and an interface module 256. The processor 252 is also coupled to the sensors 258, 270, 420A and 420B and is configured to receive signals from each sensor that are associated with the measured parameter of each respective sensor. The memory 254 is configured to store operating instructions for the processor 252 and data that may include calibration data for the sensors 258, 270, 420A, and 420B. The data may also include information such as equations or look-up tables to use the two pressure measurements from pressure sensors 420A and 420B to determine a flow rate through the porous disk 410. In certain embodiments, additional sensors, e.g., a barometric pressure transducer, outside the ventilator 100 may be used to correct the measured flow for surrounding conditions. The processor 252 is also operatively coupled to the proportional valve 300 and is capable of actuating the valve 300. The interconnection of the processor 252 with the other elements as shown in FIG. 3 may be accomplished by direct connection via any technology known to those of skill in the art, for example twisted-pair wires or fiber-optic cables, or via a network connection with microprocessors embedded in the other elements. The interface module 256 may include signal transceivers for wired or wireless communication with other devices within the ventilator 100, for example a central processor (not shown in FIG. 3), or may connect to an external interface, such as the rear interface panel 165 shown in FIG. 2B, to communicate with devices external to the ventilator 100. Interface 256 may be configured to accept both power and communication signals and, in certain embodiments, may include one or more voltage converters to provide power to the module.

Figure 4A:
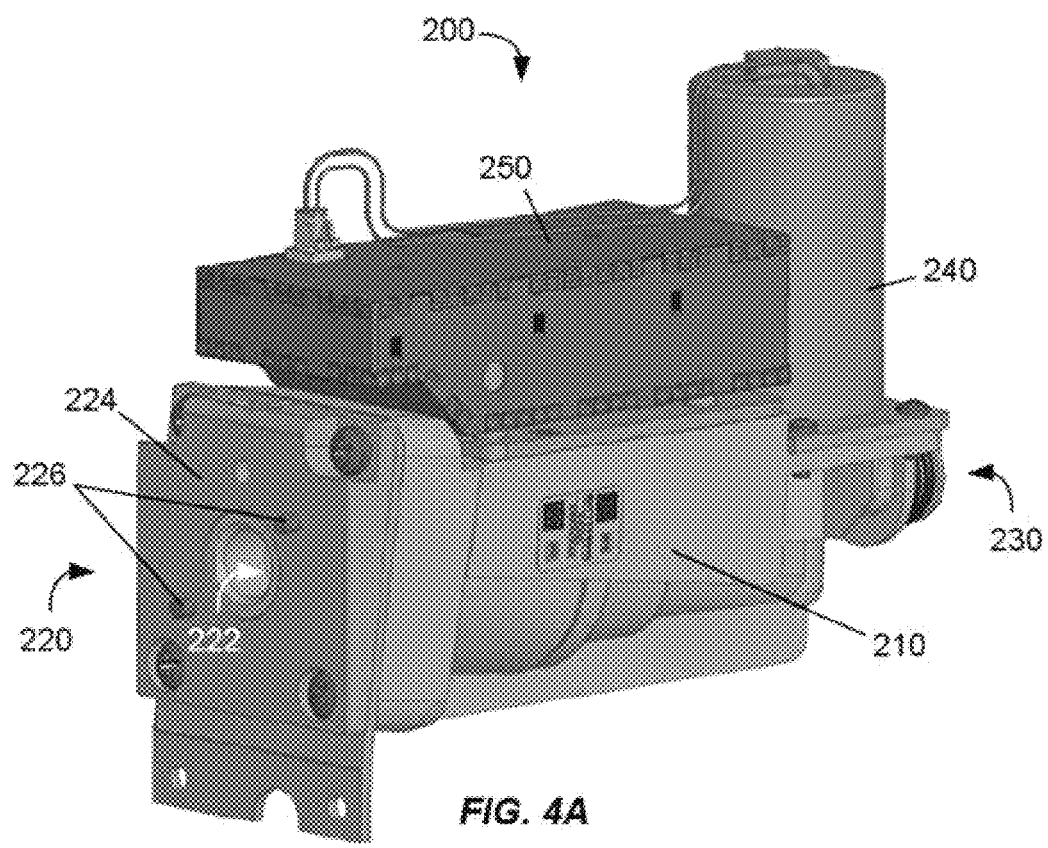
FIGS. 4A-4B depict an exemplary flow cassette according to certain aspects of the present disclosure.
Figure 4B:
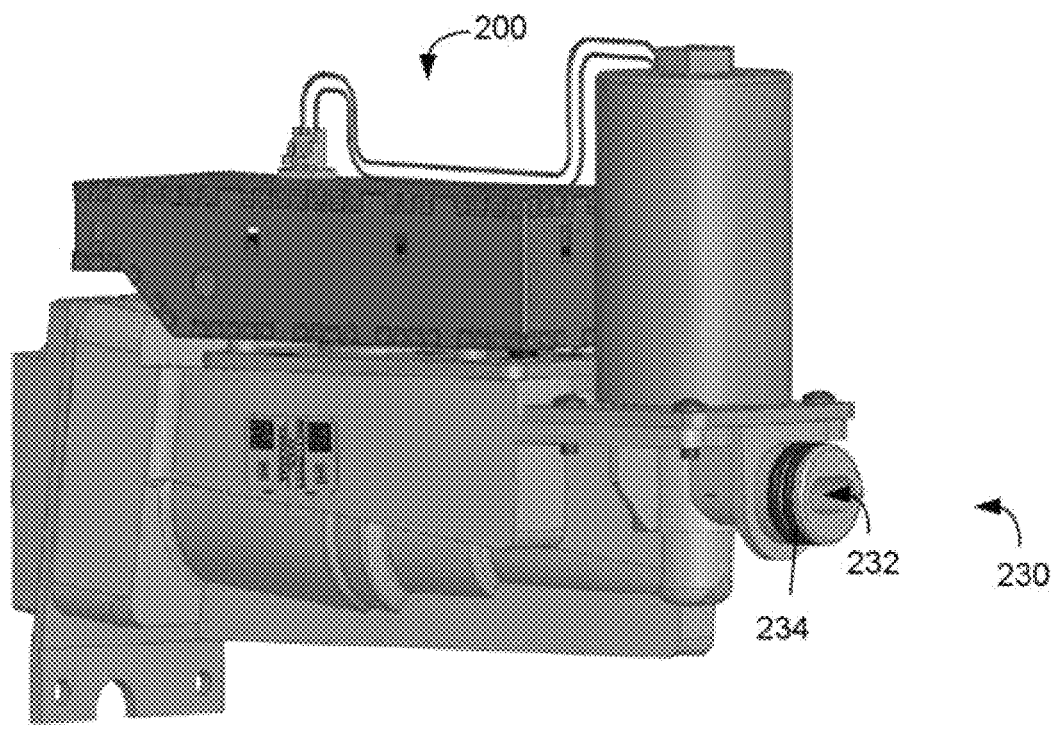

FIGS. 4A-4B depict an exemplary flow cassette 200 according to certain aspects of the present disclosure. The flow cassette 200 has a body 210 with an inlet end 220 and an outlet end 230. The inlet end 220 includes an inlet 222 that is configured to sealingly mate with a coupler 122 (not shown in FIG. 4A) of the gas inlet adapter 120. The inlet end 220 may also include locating features 226, for example protruding pins, that align the gas inlet adapter 120 to the inlet 222 and a mating face 224 that provides a reference surface for the mated gas inlet adapter 120. A solenoid 240 is attached to the body proximate to the outlet end 230 and is discussed in greater detail with respect to FIG. 5A. The electronics module 250 is attached, in this embodiment, to the top of the body 210. The details of the electronics module are discussed in greater detail with respect to FIG. 3.

FIG. 4B is a reverse-angle view of the flow cassette 200 that shows the outlet 232 and the seal 234, in this example two o-rings, that are arranged at the outlet end 230. The outlet end 230 is configured to sealingly mate with other gas passages (not shown in FIG. 4B) within the ventilator 100.

Figure 5A:
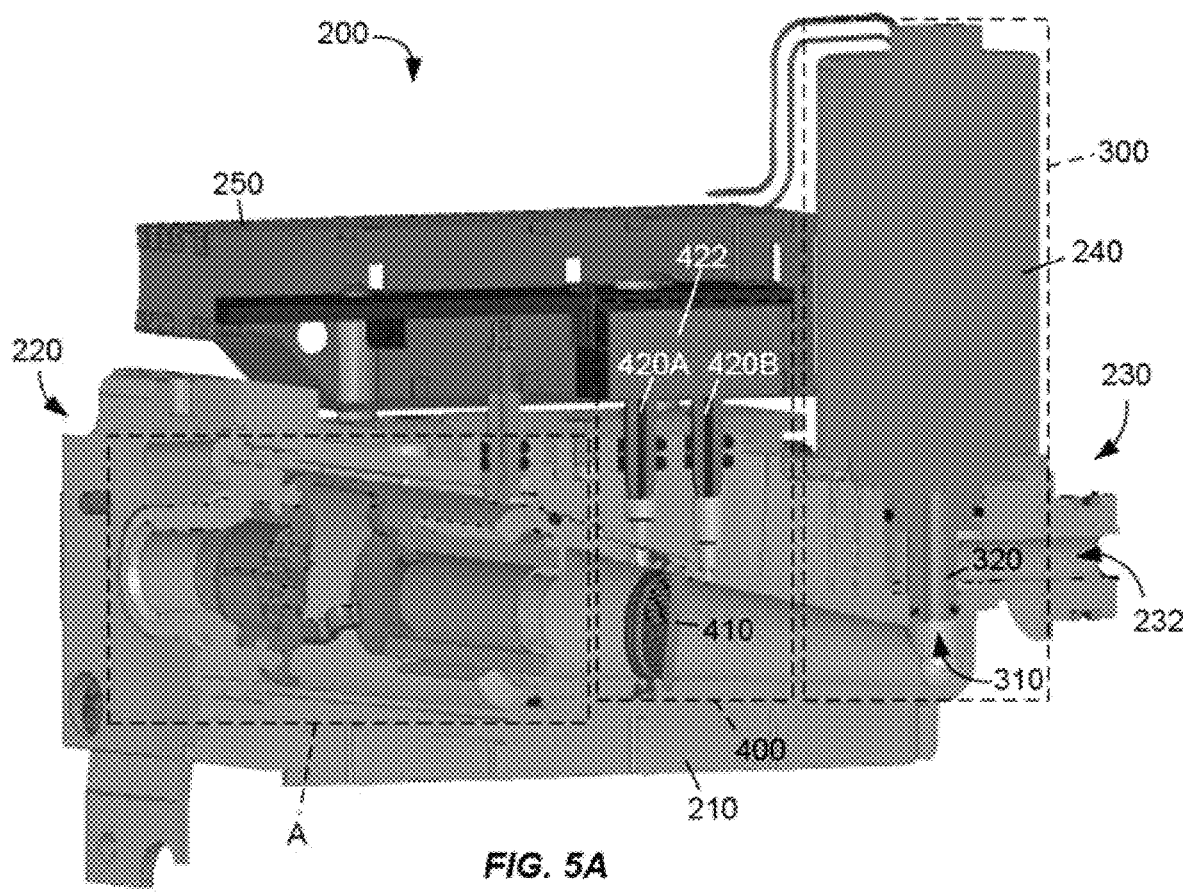
FIG. 5A is a cross-section of the flow cassette of FIGS. 4A-4B according to certain aspects of the present disclosure.

FIG. 5A is a cross-section of the flow cassette 200 of FIGS. 4A-4B according to certain aspects of the present disclosure. An enlarged view of the region indicated by the dashed-line box labeled "A" is shown in FIG. 5B.

The dashed-line box 400 indicates elements of the flow sensor 400, including the pressure sensors 420A, 420B and a flow restriction 410 that, in this example, is a porous disk. The porous disk 410 provides a known flow resistance that creates a pressure drop across the porous disk 410 that varies with flow rate and may be calibrated for one or more gases or gas mixtures. An actual pressure drop can be determined by measuring the pressures upstream and downstream of the porous disk 410 with the pressure sensors 420A and 420B and determining the pressure difference between the pressure measurements. In conjunction with the knowledge of which gas is flowing through the porous disk 410, derived from the configuration of the gas inlet adapter 120 as indicated by the magnet 128 and sensed by the Hall Effect sensor 258, and the knowledge of the temperature of the gas, as measured by the temperature sensor 270, the pressure drop can be used to determine the true flow rate, sometimes referred to as "the compensated flow rate," of the gas that is passing through the porous disk 410. The flow sensor 400 may also include pressure sensing electronics 422 that filter and condition the signals from the pressure sensors 420A, 420B and may convert the signals to digital form.

The dashed-line box 300 indicates elements of the proportional valve 300, including the solenoid 240 and a plug 320 that fits into a bore 310 of the passage 223. In certain embodiments, the plug 320 and bore 310 form an on-off fluid valve and the solenoid 240 is configured to either fully retract or fully extend the plug 320 so as to open or close the valve 300. In certain embodiments, the plug 320 and bore 310 form a variable-flow orifice and the solenoid 240 is configured to adjustably position the plug 320 with respect to the bore 310 through a feedback control loop operative within the flow cassette processor 252 that is operatively coupled to the solenoid 240. In certain embodiments, the flow cassette processor 252 may actuate the solenoid 240 so as to provide a determined flow rate, as sensed by the flow sensor 400, or a determined pressure at the outlet 232, as sensed by pressure sensor 420B.

Figure 5B:
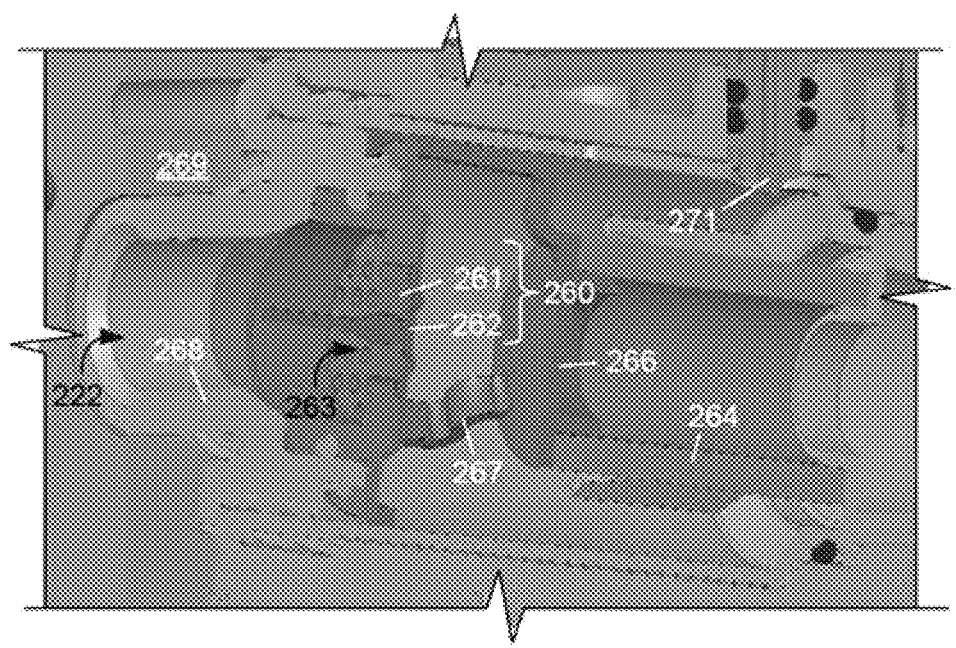
FIG. 5B is an enlarged view of a portion of FIG. 5A according to certain aspects of the present disclosure.

FIG. 5B is an enlarged view of a portion of FIG. 5A according to certain aspects of the present disclosure. Gas entering the inlet 222 passes to a check valve 260 that is configured to allow flow through the passage 223 toward the outlet 232 while resisting flow in the opposite direction. The check valve 260 includes, in this embodiment, a rigid structure 261 having a plurality of through holes 263 with a flexible disk 262 attached to the rigid structure 261 at the center. Gas flowing from the inlet towards the outlet 232 (not visible in FIG. 5B) creates a pressure on the upstream side of the flexible disk 262 that pushes the flexible disk 262 away from rigid structure 261, thereby uncovering the through holes 263 and allowing the gas to flow through the check valve 260. When the pressures on both sides of the check valve 260 equalize, the flexible disk 262 returns to sealing contact with the rigid structure 261, thereby covering the through holes 263 and preventing gas from flowing through the check valve towards the inlet 222.

After passing through the check valve 260, gas passes through a filter 264 that, in this embodiment, is formed as a hollow cylinder that is held in place by a cap 266 having legs 267 that contact the rigid structure 261 of the check valve 260 so as to retain the cap 266 and filter 264 in place. Gas passes around the outside of the cylinder and then passes inward through the filter 264 to the hollow center and then flows out of the filter 264. In certain embodiments, the filter 264 comprises a mechanical filter configured to trap particulates above a determined size. In certain embodiments, the filter 264 comprises one or more chemical filters, for example an activated charcoal or a desiccant, that are configured to absorb certain materials such as water or odors. In this embodiment, the temperature sensing element 271 is disposed proximate to the filter 264 and flush with the wall of the passage 223.

Figure 6:
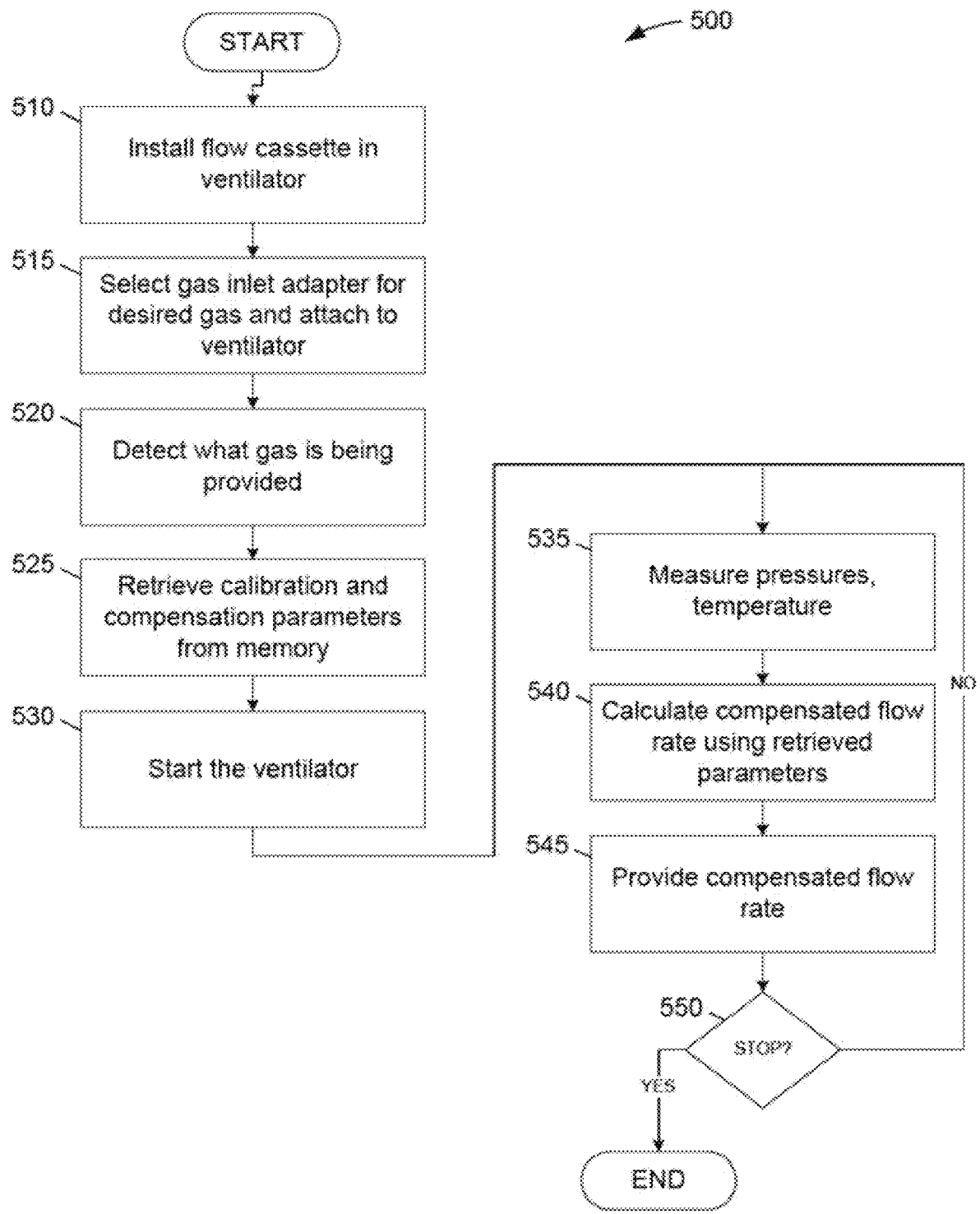
FIG. 6 is a flow chart of an exemplary configuration process according to certain aspects of the present disclosure.

FIG. 6 is a flow chart of an exemplary configuration process 500 according to certain aspects of the present disclosure. The process 500 starts in step 510 by installing a flow cassette 200 in a ventilator 100. In step 515, the user determines which gas or gas mixture, for example oxygen or heliox 70/30, will be provided to the patient, selects the proper gas inlet adapter 120, and attaches the gas inlet adapter 120 to the ventilator 100 in the proper configuration such that the correct connector of the gas inlet adapter 120 for the determined gas or gas mixture is coupled to the flow cassette 200. As the gas inlet adapter 120 includes a magnet 124 that indicates the type of gas being provided by the specific gas inlet adapter 120 as installed in the ventilator 100, the processor 252 of the flow cassette 200 can automatically determine in step 520 which gas or gas mixture is being provided by sensing the magnet 124 through the Hall Effect sensor 258, as discussed with respect to FIG. 3. In step 525, the processor 252 loads information from the memory 254 that may include calibration and/or compensation parameters related to the flow sensor 400. The ventilator 100 is now configured for use. After the user connects a breathing circuit with a patient, generally as shown in FIG. 1, the user starts the ventilator 100 in step 530.

During operation of the ventilator 100, the flow cassette 200 measures the pressures on both sides of the porous disk 410 and the temperature of the gas passing through the flow cassette 200 in step 535 using the flow sensor 400 and temperature sensor 270, respectively, as described with respect to FIGS. 3 and 5A. In step 540, the processor 252 applies the compensation and calibration information downloaded in step 525 to calculate the actual flow rate of the gas and provides this flow rate information in step 545, for example to a processor in the ventilator 100. Step 550 is a decision point that branches depending on whether a "stop" command has been received. If the user has provided a "stop" command, the process 500 branches along the "yes" path to the end and terminates. IF the user has not provided a "stop" command, the process 500 branches along the "no" path back to step 535 and measures the pressures and temperature. The process 500 will loop through the steps 535-550 until a "stop" command is received.

In summary, it can be seen that the disclosed embodiments of the flow cassette consolidate certain mechanical functions, such as backflow prevention and filtration, and the sensing of certain parameters, such as flow rate, in a compact and modular form. In certain embodiments, the flow cassette includes electronics that process the raw measurements using internally stored compensation and calibration data and provide more accurate values of the sensed parameters. In certain embodiments, the flow cassette may be configured to provide either a determined pressure or a determined flow rate of the supply gas at the outlet. The modular form enables this subsystem to be independently tested and calibrated as well as simplifying assembly and replacement.

The previous description is provided to enable any person skilled in the art to practice the various aspects described herein. While the foregoing has described what are considered to be the best mode and/or other examples, it is understood that various modifications to these aspects will be readily apparent to those skilled in the art, and the generic principles defined herein may be applied to other aspects. Thus, the claims are not intended to be limited to the aspects shown herein, but is to be accorded the full scope consistent with the language claims, wherein reference to an element in the singular is not intended to mean "one and only one" unless specifically so stated, but rather "one or more." Unless specifically stated otherwise, the terms "a set" and "some" refer to one or more. Pronouns in the masculine (e.g., his) include the feminine and neuter gender (e.g., her and its) and vice versa. Headings and subheadings, if any, are used for convenience only and do not limit the invention.

To the extent that the terms "include," "have," or the like are used in the description or the claims, such terms are intended to be inclusive in a manner similar to the term "comprise" as "comprise" is interpreted when employed as a transitional word in a claim.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

Terms such as "top," "bottom," "front," "rear" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

A phrase such as an "aspect" does not imply that such aspect is essential to the subject technology or that such aspect applies to all configurations of the subject technology. A disclosure relating to an aspect may apply to all configurations, or one or more configurations. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. A phrase such an embodiment may refer to one or more embodiments and vice versa.

The word "exemplary" is used herein to mean "serving as an example or illustration." Any aspect or design described herein as "exemplary" is not necessarily to be construed as preferred or advantageous over other aspects or designs.

No claim element is to be construed under the provisions of 35 U.S.C. § 112, sixth paragraph, unless the element is expressly recited using the phrase "means for" or, in the case of a method claim, the element is recited using the phrase "step for."

What is claimed is:

1. A flow cassette adapted for use in a ventilator comprising:
   a housing having an inlet and an outlet with a passage therebetween;
   a check valve within the passage, the check valve configured to resist a flow of fluid toward the inlet;
   a filter positioned within the passage, and between the check valve and the outlet; and
   a cap engaged against the filter and comprising a leg that extends toward an inner surface of the passage such that a first end portion of the filter is concentrically located within the passage.

2. The flow cassette of claim 1, wherein the leg extends toward the check valve such that the filter is spaced apart from the check valve.

3. The flow cassette of claim 1, comprising a flow rate sensor positioned within the passage and configured to measure a flow rate of the fluid flowing through the passage, wherein the flow rate sensor comprises a flow restriction, a first pressure sensor positioned between the flow restriction and the inlet, and a second pressure sensor positioned between the flow restriction and the outlet.

4. The flow cassette of claim 3, wherein the first pressure sensor positioned between the flow restriction and a second end portion of the filter.

5. The flow cassette of claim 1, comprising a temperature sensor disposed within the passage and configured to measure a temperature of a fluid flowing through the passage.

6. The flow cassette of claim 1, comprising a processor coupled to a temperature sensor and a flow rate sensor, the processor configured to accept measurements of the temperature and the flow rate from the temperature sensor and flow rate sensor, respectively, and provide a compensated flow rate.

7. The flow cassette of claim 1, comprising a valve positioned within the passage and configured to provide a selectable flow restriction so as to maintain one of a determined flow rate and a determined pressure at the outlet.

8. A flow cassette adapted for use in a ventilator comprising:
 a housing having an inlet and an outlet with a passage therebetween;
 a check valve positioned within the passage;
 a filter positioned within the passage, and between the check valve and the outlet; and
 a cap engaged against the filter, wherein the cap is positioned between the check valve and the filter within the passage.

9. The flow cassette of claim 8, wherein the cap comprises a leg extending between the check valve and the filter such that the filter is spaced apart from the check valve.

10. The flow cassette of claim 9, wherein the check valve comprises a flexible disk positioned between a rigid structure of the check valve and the filter, and wherein the flexible disk obstructs a flow from the outlet toward the inlet.

11. The flow cassette of claim 8, wherein the check valve comprises a rigid structure having a plurality of passages.

12. The flow cassette of claim 8, wherein the filter comprises a cylindrical cross-sectional profile having an inner passage.

13. The flow cassette of claim 12, wherein the cap engages a first end portion of the filter such that a gas, moving from the inlet toward the outlet, is directed through an outer surface of the filter toward the inner passage.

14. The flow cassette of claim 8, comprising a temperature sensor positioned within the passage and configured to measure a temperature of a fluid flowing through the passage.

15. The flow cassette of claim 8, comprising a flow rate sensor positioned within the passage and configured to measure a flow rate of a fluid flowing through the passage.

16. The flow cassette of claim 15, wherein the flow rate sensor comprises a flow restriction.

17. The flow cassette of claim 16, wherein the flow rate sensor comprises a first pressure sensor positioned between the flow restriction and the inlet, and a second pressure sensor positioned between the flow restriction and the outlet.

18. The flow cassette of claim 8, comprising a processor coupled to a temperature sensor and a flow rate sensor, the processor configured to accept measurements of the temperature and the flow rate from the temperature sensor and flow rate sensor, respectively, and provide a compensated flow rate.

19. The flow cassette of claim 8, comprising a valve positioned within the passage and configured to provide a selectable flow restriction so as to maintain one of a determined flow rate and a determined pressure at the outlet.

* * * * *